US00PP27865P3

(12) United States Plant Patent
Carruth

(10) Patent No.: US PP27,865 P3
(45) Date of Patent: Apr. 11, 2017

(54) GRANDIFLORA ROSE PLANT NAMED 'WEKDOOFAT'

(50) Latin Name: *Rosa hybrida*
Varietal Denomination: WEKdoofat

(71) Applicant: Early Morning LLC, Pomona, CA (US)

(72) Inventor: Thomas F. Carruth, Altadena, CA (US)

(73) Assignee: Early Morning LLC, Pomona, CA (US)

( * ) Notice: Subject to any disclaimer, the term of this patent is extended or adjusted under 35 U.S.C. 154(b) by 8 days.

(21) Appl. No.: 14/544,115

(22) Filed: Nov. 25, 2014

(65) Prior Publication Data

US 2016/0150691 P1 May 26, 2016

(51) Int. Cl.
*A01H 5/02* (2006.01)

(52) U.S. Cl.
USPC ..... Plt./135

(58) Field of Classification Search
USPC ..... Plt./130, 135, 136, 146, 147, 105, 106
See application file for complete search history.

(56) References Cited

U.S. PATENT DOCUMENTS

PP6,121 P 3/1988 Christensen
PP17,305 P2 12/2006 Carruth

OTHER PUBLICATIONS

Greenleaf Nursery retrieved on Apr. 21, 2016, retrieved from the Internet at <http://www.greenleafnursery.com/index.cfm/fuseaction/plants.plantDetail/plant_id/6822/index.htm> one page.*
Siktberg Greenhouse Grower 2013 retrieved on Apr. 21, 2016, retrieved from the Internet at <http://www.greenhousegrower.com/varieties/weeks-roses-to-breed-new-rose-varieties-inspired-by-downton-abbey/> 5 pp.*
Weeks Roses, 2015 Wholesale Rose Catalog, 84 pages.
Fact Sheet for Anna's Promise 2015, 1 page.

* cited by examiner

*Primary Examiner* — June Hwu
(74) *Attorney, Agent, or Firm* — McKee, Voorhees & Sease, PLC

(57) ABSTRACT

A new variety of Grandiflora rose suitable for garden decoration, having flowers of golden tan with copper reverse coloration.

1 Drawing Sheet

Classification: The present invention relates to a new *Rosa hybrida* plant.

Variety denomination: The new plant has the varietal denomination 'WEKdoofat'.

BACKGROUND OF THE INVENTION

This invention relates to a new and distinct variety of Grandiflora Rose. It has as its seed parent the variety known as 'AROmiclea' (U.S. Plant Pat. No. 6,121) and as its pollen parent the variety known as 'WEKosupalz' (U.S. Plant Pat. No. 17,305).

SUMMARY OF THE INVENTION

Among the features which distinguish the new variety from other presently available and commercial rose cultivars known to the inventor are the following combinations of characteristics: its unique flowers of golden tan with copper reverse coloration, its many hairs on the peduncle and its red suffusion on both sides of the attachment point on the upper surface of the petal. The plant has an upright moderately spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKdoofat' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'AROmiclea' by the following combination of characteristics: whereas 'WEKdoofat' bears moderately large sized flowers (about 7.6 to about 11.2 cm. in diameter) of golden tan with copper reverse coloration, 'AROmiclea' bears significantly larger flowers (about 11.5 to about 14.0 cm. in diameter) of chatoyant orange coloration. The new variety is classified as a Grandiflora rose with an upright moderately spreading medium height growing habit (about 160 to about 190 cm. in height and about 150 to about 180 cm. spread at the widest point), whereas the seed parent is classified as a Hybrid Tea rose with a taller and less spreading growing habit.

The new variety may be distinguished from its pollen parent, 'WEKosupalz' by the following combination of characteristics: whereas 'WEKdoofat' bears moderately large sized flowers (about 7.6 to about 11.2 cm. in diameter) of golden tan with copper reverse coloration, 'WEKosupalz' bears larger flowers (about 10.0 to about 13.1 cm. in diameter) of golden orange coloration with a bronzy red reverse. The new variety has an upright moderately spreading medium height growing habit (about 160 to about 190 cm. in height and about 150 to about 180 cm. spread at the widest point), whereas the pollen parent has a very upright taller and significantly less spreading growing habit (about 170 to about 200 cm. in height and about 92 to about 108 cm. spread at the widest point).

COMPARISON WITH THE CLOSEST COMMERCIALLY AVAILABLE CULTIVAR

The closest commercially available cultivar to the new variety is the pollen parent 'WEKosupalz' (U.S. Plant Pat. No. 17,305).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of November.

Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety usually bears its flowers singly, sometimes in clusters of two to three per stem. Flowers may be borne in regular rounded clusters on strong short to medium length stems (about 16 to about 42 cm.). Flowers are an average of 6.5 to 7.5 cm. in height. Outdoors, the plant blooms abundantly and nearly continuously during the growing season. The flowers have a moderate fruity to slightly spicy fragrance.

BUD

The peduncle is about 3.4 to about 8.7 cm. in length, of average to somewhat heavy caliper (about 0.3 to about 0.4 cm. in diameter) and usually erect. It is smooth, with many hairs. Peduncle color is between 146C and 137B often lightly suffused, especially on the side exposed to the sun, with between 187B and 187C.

Before the calyx breaks, the bud is about 1.2 to about 2.2 cm. in diameter at the widest point, about 1.5 to about 2.4 cm. in length, and pointed to somewhat ovoid in shape. The surface of the bud bears between 14 to 25 foliaceous appendages total per flower and an average of 0-7 foliaceous appendages per sepal. The bud bears few stipitate glands and hairs, usually with moderately stout, much-cut, foliaceous parts extending beyond the tip of the bud about ¾ or more of its length. Bud color is between 146B and 137B often moderately suffused, especially on the side exposed to the sun, with between 187A and 187B.

The sepals are about 2.2 to about 5.1 cm. in length and about 0.9 to about 1.4 cm. in width at the widest point. The outer surface color of the sepal is between 146B and 137B often moderately suffused, especially on the side exposed to the sun, with between 187A and 187B. The outer surface of the sepal is smooth and bears between 0 to 7 foliaceous appendages with few stipitate glands and hairs. The inner surface color of the sepal is near 146C broadly bordered by near 137C. After the sepals open, the inner surface color is often heavily suffused, especially on the area exposed to the sun, with between 187A and 187B. The inner surface of the sepal is covered with fine wooly tomentum; sepal margins are lined with few stipitate glands and some hairs.

The receptacle of the flower is of medium length (about 0.7 to about 0.9 cm.) and somewhat thin to average in caliper (about 0.8 to about 1.1 cm. in diameter). The receptacle is urn-shaped in form. Its surface is smooth with some hairs and with thick fleshy walls. The receptacle color is between 144A and 137A.

As the petals open (after the calyx breaks), the bud is about 1.8 to about 2.4 cm. in diameter at the widest point, about 2.4 to about 3.6 cm. in length, and pointed to somewhat ovoid in form. The color of the under surfaces of the newly opened petals is between 46B and 46C sometimes moderately suffused with between 187A and 187B. At the point where the petal attaches, there is a small zone of between 154C and 151C. The color of the upper surfaces of the newly opened petals is between 35A and 34B sometimes moderately suffused with between 53B and 53A. At the point where the petal attaches, there is a large zone of near 13B suffused on both sides with between 53A and 53B.

BLOOM

When fully open, the bloom ranges from about 7.6 to about 11.2 cm. in diameter. Petalage is double with about 25 to 32 petals and about 4 to 6 petaloids irregularly arranged. When partially open, the bloom form is high centered to moderately cupped, and the petals are loosely spiraled to somewhat cupped with petal edges slightly reflexed outward. When fully open, the bloom form is more cupped, and the petals are loosely cupped to moderately undulated with petal edges moderately reflexed to somewhat rolled outward.

PETALS

The substance of the petals is slightly heavy and of somewhat thin to medium thickness, with upper surfaces slightly satiny and under surfaces somewhat shiny to matte. The petals are about 4.3 to about 5.4 cm. in length and about 3.8 to about 5.6 cm. in width at the widest point. Petal margins are entire.

The outer petals are somewhat obovate to nearly rounded in shape with rounded apices and sometimes slightly notched with one to two notches.

The inner petals are moderately obovate in shape with rounded apices.

Petaloids are about 1.6 to about 4.4 cm. in length and about 0.6 to about 4.5 cm. in width at the widest point. Petaloids are shaped moderately obovate to somewhat oblanceolate with rounded apices.

NEWLY OPENED FLOWER

The under surface color of the outer petals is between 52A and 50B sometimes moderately suffused with between 187D and 60A. At the point where the petal attaches, there is a small zone of near 13C. The upper surface color of the outer petals is between 24C and 24D often moderately suffused with between 53B and 53C. At the point where the petal attaches, there is a large zone of between 14C and 13C suffused on both sides with between 53A and 53B.

The under surface color of the intermediate and inner petals is between 47D and 50B. The upper surface color of the intermediate and inner petals is between 24C and 24D often lightly suffused with between 53B and 53C.

The under and upper surface colors of the petaloids are similar in coloration to the upper and under surfaces of the intermediate and inner petals.

The general tonality of the newly opened flower is between 24C and 24D often lightly suffused with between 53B and 53C.

THREE-DAY-OLD FLOWER

The under surface color of the outer petals is between 54B and 48B sometimes moderately suffused with 60A and 60B. At the point where the petal attaches, there is a small zone of between 8B and 10B. The upper surface color of the outer petals is between 19B and 24D often heavily suffused with between 60C and 60D. At the point where the petal attaches, there is a large zone of near 14D suffused on both sides with near 53C.

The under surface color of the intermediate and inner petals is between 48C and 48B. The upper surface color of the intermediate and inner petals is between 19B and 24D often moderately suffused with between 60C and 60D.

The under and upper surface colors of the petaloids are similar in coloration to the upper and under surfaces of the intermediate and inner petals.

The general tonality of the three-day-old flower is between 19B and 24D often moderately suffused with between 60C and 60D.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 140) and are arranged regularly about the pistils; a few are mixed with petaloids. The filaments are of medium to somewhat long length (about 0.5 to about 1.0 cm.) most with anthers. Filaments are between 12A and 13B in color. The anthers are somewhat small for the class and all open approximately at the same time. Anther color when immature is near 21B on the external part and near 13D on the internal part. Anther color at maturity is near 163A on the external part and near 200A on the internal part. Pollen is moderate and between 19C and 18C in color.

FEMALE REPRODUCTIVE ORGANS

Pistils vary in number (average about 95). The styles are moderately even, somewhat long in length (about 0.4 to about 0.9 cm.), moderately thin in caliper, and loosely bunched to somewhat separated. Stigma color is near 11A. Style color is between 1C and 154C. Ovaries are usually all enclosed in the calyx.

Hips are of somewhat short to average length (about 1.5 to about 2.0 cm.), rounded in form with a flat top and flat base, and between 28A and 30C in color when ripe. The hip surface is smooth with thick fleshy walls. The sepals are moderately fugacious and usually straight in shape.

The seeds are irregularly rounded, smooth in texture, approximately 8 to about 13 per hip, about 0.4 to about 0.6 cm. in diameter at the widest point and between 164C and 165C in color.

FOLIAGE

The compound leaves are usually comprised of three to seven leaflets and are borne abundantly. The five-leaflet leaves are about 10.7 to about 17.1 cm. in length and about 8.4 to about 15.3 cm. in width at the widest point, leathery to somewhat crisp in texture, and glossy in finish on the upper side and somewhat glossy to matte in finish on the under side. The leaves have a pinnate venation pattern. The terminal leaflets are about 5.0 to about 9.3 cm. in length and about 3.6 to about 6.2 cm. in width at the widest point, shaped moderately oval to somewhat ovate with acuminate apices and rounded bases. Their margins are usually simply serrate.

The upper surface color of the mature leaf is between 147A and 139A. The under surface color of the mature leaf is between 147B and 137C. The under and upper colors of the leaf veins on the mature leaf are similar in coloration to the upper and under surfaces colors of the mature leaf. The upper surface color of the young leaf is between 137A and 146A, often heavily suffused with between 187A and 183A. The under surface color of the young leaf is between 146C and 137B, often heavily suffused with between 187A and 187B. The under and upper colors of the leaf veins on the young leaf are similar in coloration to the upper and under surfaces colors of the young leaf.

The rachis is somewhat light in caliper and rough. The upper side is shallowly grooved with few hairs and some stipitate glands on the edges of the grooves. The under side of the rachis is rough with some stipitate glands and few small prickles. The rachis color is near 146C on the under side and near 137B on the upper side often moderately suffused on the young leaves with between 187B and 187C.

The stipules are about 1.5 to about 2.1 cm. in length and of somewhat narrow to medium width (about 0.4 to about 0.7 cm.) with short straight points that usually turn out at an angle of more than 45 degrees and sometimes recurve toward the stem. The under and upper surface color of the stipule is between 137A and 137B sometimes moderately suffused on the young leaves with between 187B and 187C.

The petiole is somewhat light in caliper and rough. The upper side is shallowly grooved with few hairs and some stipitate glands on the edges of the grooves. The under side of the petiole is rough with some stipitate glands and few small prickles. The petiole is about 0.6 to about 1.8 cm. in length and about 0.1 to about 0.2 cm in width at the widest point. The petiole color is near 146C on the under side and near 137B on the upper side often moderately suffused on the young leaves with between 187B and 187C.

The plant displays an average degree of resistance to powdery mildew and rust as compared to other commercial varieties grown under comparable conditions in Pomona, Calif. The plant's winter hardiness and drought/heat tolerance are yet to be determined.

GROWTH

The plant has an upright moderately spreading medium height growing habit (about 160 to about 190 cm. in height and about 150 to about 180 cm. spread at the widest point), with full branching. It displays moderately vigorous growth and the canes are of medium caliper for the class (about 2.4 to about 3.0 cm. in diameter at the widest point).

The color of the major stems is between 146A and 147B. They bear some large prickles that are about 0.4 to about 0.6 cm. in length. The large prickles are hooked moderately downward with a long narrow oval base; prickle color is between 200C and 165A often moderately suffused with between 201A and 201B. The major stem bears many small prickles of similar shape and coloration.

The color of the branches is between 146A and 147A. They bear some large prickles which are of similar size and shape to the large prickles on the major stems; prickle color is between 200C and 165A. The branches bear many small prickles of similar shape and coloration.

The color of the new shoots is between 146B and 146A often moderately suffused with between 187B and 187C. They bear some large prickles which are of similar size and shape to the large prickles on the major stems; prickle color is between 152D and 153A often moderately suffused with between 187C and 187D. The shoots bear many small prickles of similar shape and coloration.

I claim:

1. A new and distinct Grandiflora rose plant of the variety substantially as described and illustrated herein.

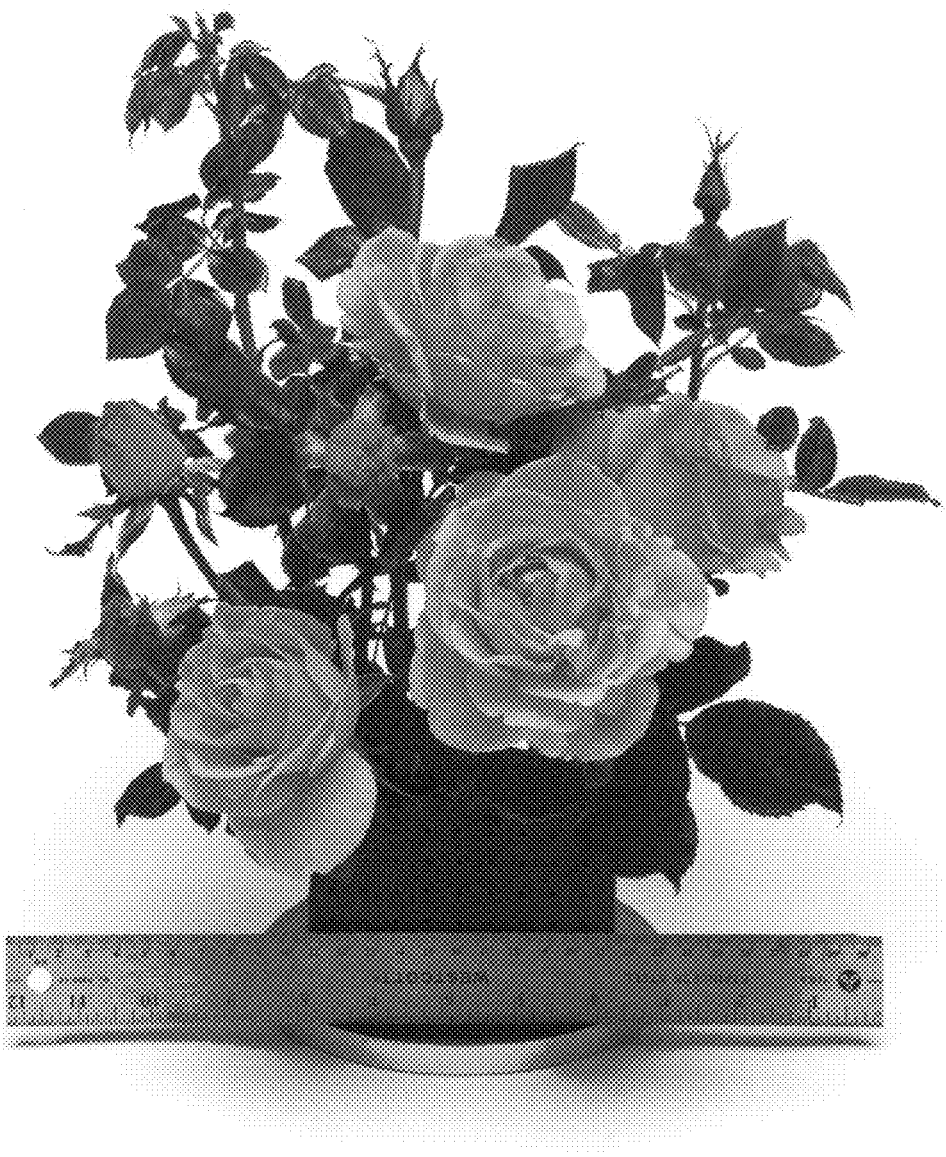

* * * * *